(12) United States Patent
Morana et al.

(10) Patent No.: US 11,344,550 B2
(45) Date of Patent: May 31, 2022

(54) PROCESS FOR THE PREPARATION OF THE CRYSTALLINE FORM III OF TIPIRACIL HYDROCHLORIDE

(71) Applicant: Procos S.P.A., Cameri (IT)

(72) Inventors: Fabio Morana, Novara (IT); Stefano Gobbato, Cameri (IT); Lucia Cozzi, Brescia (IT); Jacopo Roletto, Turin (IT); Paolo Paissoni, Druento (IT)

(73) Assignee: Procos S.P.A., Cameri (IT)

( * ) Notice: Subject to any disclaimer, the term of this patent is extended or adjusted under 35 U.S.C. 154(b) by 217 days.

(21) Appl. No.: 16/760,685

(22) PCT Filed: Oct. 23, 2018

(86) PCT No.: PCT/EP2018/078964
§ 371 (c)(1),
(2) Date: Apr. 30, 2020

(87) PCT Pub. No.: WO2019/086292
PCT Pub. Date: May 9, 2019

(65) Prior Publication Data
US 2020/0330465 A1    Oct. 22, 2020

(30) Foreign Application Priority Data
Nov. 2, 2017   (IT) .................. 102017000124805

(51) Int. Cl.
*C07D 403/06*   (2006.01)
*A61K 31/513*   (2006.01)

(52) U.S. Cl.
CPC .................. *A61K 31/513* (2013.01)

(58) Field of Classification Search
CPC ................. C07B 2200/13; C07D 403/06
See application file for complete search history.

(56) References Cited

U.S. PATENT DOCUMENTS

2020/0283414 A1 *  9/2020  Sukumar .............. C07D 403/06

FOREIGN PATENT DOCUMENTS

| CN | 106333952 A | 1/2017 | |
| EP | 3012255 A1 * | 4/2016 | ............. A61P 43/00 |
| EP | 3012255 A1 | 4/2016 | |
| WO | WO-2019053574 A1 * | 3/2019 | ........... C07D 403/06 |

OTHER PUBLICATIONS

Anonymous "Process of preparation of Crystal III of 5-Chloro-6-[(2-imino-1-pyrrolidinyl)methyl]-2,4(1 H,3H)-pyrimidinedione hydrochloride having low content of residual solvent" IP.com Journal (Jun. 20, 2017) (Year: 2017).*
Anonymous "Process of the preparation of Crystal III of 5-Chloro-6-[(2-imino-1-pyrrolidinyl)methyl]-2,4(1H, 3H)-pyrimidinedione hydrochloride having a low content of residual solvent", IP.Com Journal, Jun. 20, 2017.
International Preliminary Report on Patentability of PCT/EP2018/078964 dated Dec. 18, 2019.
Search Report and Written Opinion of PCT/EP2018/078964 dated Jan. 8, 2019.

* cited by examiner

*Primary Examiner* — Amanda L. Aguirre
(74) *Attorney, Agent, or Firm* — Silvia Salvadori, P.C.; Silvia Salvadori

(57) ABSTRACT

The present invention concerns a process for the preparation of the crystalline form III of Tipiracil hydrochloride having a content of residual solvents lower than the ICH limits. Said process is advantageous with respect to the known processes because it allows the production of the form III of Tipiracil hydrochloride suitable for use in the preparation of pharmaceutical finished products.

3 Claims, 1 Drawing Sheet

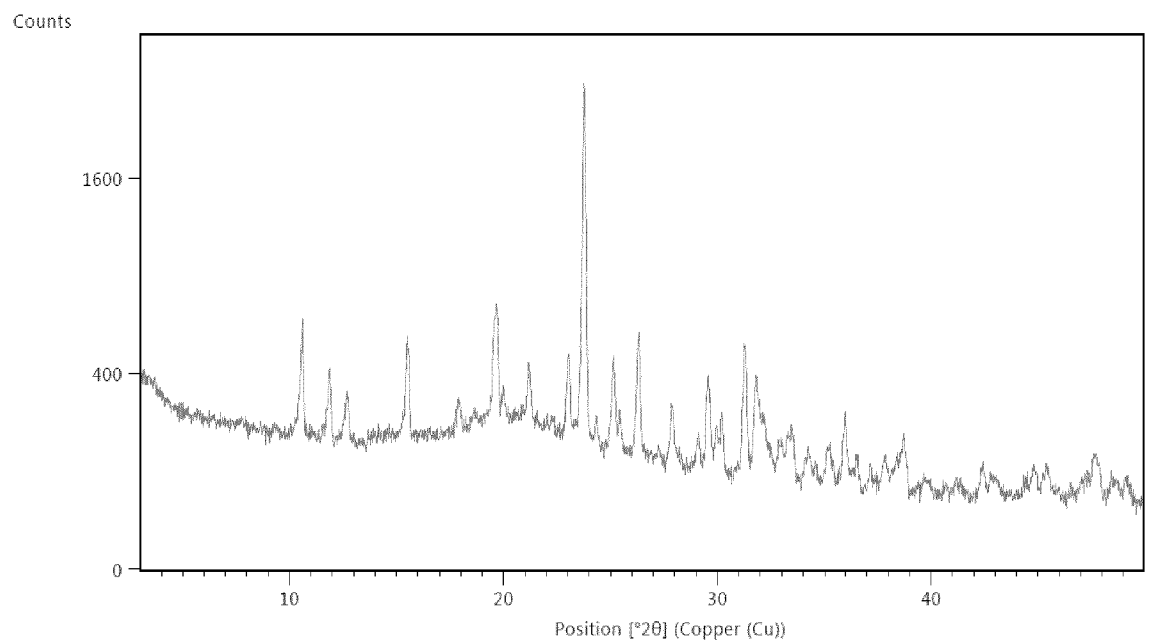

PROCESS FOR THE PREPARATION OF THE CRYSTALLINE FORM III OF TIPIRACIL HYDROCHLORIDE

This application is a U.S. national stage of PCT/EP2018/078964 filed on 23 Oct. 2018, which claims priority to and the benefit of Italian Application No. 102017000124805 filed on 2 Nov. 2017, the contents of which are incorporated herein by reference in their entireties.

FIELD OF THE INVENTION

The present invention relates to a process for the preparation of the crystalline form III of Tipiracil hydrochloride having a content of residual solvents lower than the ICH limits, as well as the pharmaceutical use of said crystalline form III.

BACKGROUND OF THE INVENTION

Tipiracil hydrochloride (5-Chloro-6-[(2-imino-1-pyrrolidinyl)methyl]-2,4(1H,3H)-pyrimidinedione (Formula 1), is an active pharmaceutical ingredient (API) used in combination with trifluridine as an antitumor medicament for the treatment of colorectal metastatic carcinoma.

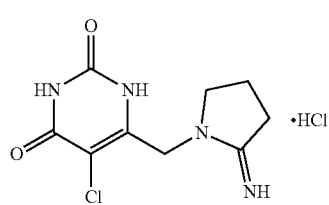

(1)

WO9630346 discloses Tipiracil hydrochloride without providing any information about the physical state of the API and about its polymorphism.

Bioorganic & Medicinal Chemistry (2004), 12(13), 3443-3450 discloses Tipiracil hydrochloride in the form of white crystals having a melting point of 245° C.

EP 3012255 A1 discloses three different crystalline forms of Tipiracil hydrochloride, named form I, II and III, and the process for their preparation.

The powder X-ray diffraction pattern of Form I shows characteristic peaks at angles of 11.6°, 17.2°, 17.8°, 23.3°, 27.1°, and 29.3° as a diffraction angle (2θ±0.1°).

The powder X-ray diffraction pattern of Form II shows characteristic peaks at angles of 6.5°, 20.6°, 25.5°, 26.1°, 27.0°, and 30.2° as a diffraction angle (2θ±0.1°).

The powder X-ray diffraction pattern of Form III shows characteristic peaks at angles of 10.5°, 19.6°, 23.7°, 26.2°, and 31.2° as a diffraction angle (2θ±0.1°).

According to the crystallization procedures disclosed in EP 3012255 A1, the three different crystalline forms are obtained from mixtures of water and ethanol, by proper variation of the time and the temperature of crystallization: the crystalline form I is obtained at temperatures higher than 40° C. and subsequent cooling; the crystalline form II is obtained at temperatures not higher than 40° C., whereas the crystalline form III is obtained according two protocols that use aqueous HCl and an organic solvent selected form ethanol and methanol. In both procedures, the value of the residual organic solvent present in the crystal of form III is far above the specification limits recommended by the ICH guidelines for an API.

According to the disclosure of EP 3012255 A1, the crystalline forms I and III are endowed with stability to light, oxygen, humidity, and heating which is higher than that of the crystalline form II; however, the crystalline form III has a content of residual solvents higher than that of the crystalline form I, which content is conflicting with the ICH guidelines for use in medicinal products.

CN106333952A discloses a process in which Tipiracil hydrochloride of an unspecified crystalline form, previously obtained by dissolution of Tipiracil free base in hydrochloric acid at 75-80° C. and subsequent precipitation at 2-8° C., is dissolved again by heating in a mixture of water-organic solvent. The subsequent new cooling leads to the precipitation of crystals of the form I of Tipiracil hydrochloride, as explicitly stated in all of examples of this document.

IP.com Journal, 20 June 2017, XP013175208, ISSN: 1533-0001, discloses a process for the preparation of form III of Tipiracil hydrochloride, which is stated to have a low content of residual solvents. Actually, as it will be shown below in the comparative example 1 of the present invention performed on the same scale, said process does not lead to a crystalline form III of Tipiracil hydrochloride having a content of residual solvents below the limits set by the ICH guidelines.

DESCRIPTION OF THE FIGURE

The FIG. 1 shows the X-ray diffraction pattern of the form III of Tipiracil hydrochloride obtained according to Example 2 of the present invention.

DESCRIPTION OF THE INVENTION

It has now been found that the crystalline form III of Tipiracil hydrochloride can be obtained having a content of residual solvents that is compatible with its use as a medicament, in particular having a content of solvents in compliance with the ICH guidelines, using a process that allows its production on an industrial scale.

The crystalline form III of Tipiracil hydrochloride, hereinafter form III, can be obtained either from the crystalline form II of Tipiracil hydrochloride, hereinafter form II, or from Tipiracil free base, using isopropanol.

The reaction can be performed at a temperature between 0° C. and the boiling point of the solvent, preferably between 20 and 60° C.

According to a preferred embodiment, the process of the invention is carried out as described in the following, wherein the order of addition of the raw materials may also differ.

Typically, the form II, obtained according to known procedures by means of dissolution-concentration from water that allows the removal initially of particulate matter and of foreign bodies by treatment of the aqueous solution with activated carbons, and then of water soluble impurities, is suspended in isopropanol, preferably in 6-10 volumes; the solution is stirred, preferably for 1-24 hours, more preferably for 12-24 hours, at a temperature between 20 and 60° C. At the end of the heating period, the suspension is filtered to yield form III of the invention.

Alternatively, form III of the invention can be obtained from the free base of Tipiracil, prepared according to known procedures. The free base, after dissolution in aqueous HCl and removal of particulate matter and foreign bodies by treatment of the aqueous solution with active carbons, is concentrated to dryness at a temperature between 0 and 40° C., preferably between 25 and 30° C. Isopropanol, preferably 6-10 volumes, is then added. The solution is then stirred, preferably for 1-24 hours, more preferably for 12-24 hours, at a temperature between 0° C. and the boiling point of the solvent, preferably 20-60° C. At the end of the heating period, the suspension is filtered to yield form III.

From the X-ray diffraction pattern, the solid obtained according to the two above-described procedures consists exclusively of the form III.

The analysis of the residual water content through Karl Fischer titration is fully consistent with the obtainment of an anhydrous form, such as form III.

In addition, the gas chromatographic (GC) analysis according to the head space method shows that the content of residual solvents is below the limits (5000 ppm for isopropanol) set by the current ICH guidelines.

The form III of the present invention is therefore particularly useful for the preparation of pharmaceutical compositions.

The form III of the present invention for pharmaceutical use is a further object of the invention.

The invention is illustrated in detail by the following examples.

EXAMPLES

Example 1: Preparation of Form III of Tipiracil Hydrochloride Having a Content of Residual Solvents Below the ICH Limits, Starting from Tipiracil Hydrochloride Form II 10 g of form II, obtained according to reference example 1 of EP3012255, are suspended in 50 mL of isopropanol and the suspension is stirred at 25° C. for 24 h before being filtered.

8.5 g of form III of Tipiracil hydrochloride are obtained (content of residual water according to Karl Fischer titration: 0.37%; content of residual solvents according to GC analysis (head space): 3540 ppm<5000 ppm, ICH limit).

Example 2: Preparation of Form III of Tipiracil Hydrochloride Having a Content of Residual Solvent Below the ICH Limits, Starting from the Free Base of Tipiracil Obtained According to WO 96/30346

10 g of the free base of Tipiracil (IUPAC name: 5-chloro-6-((2-iminopyrrolidin-1-yl)methyl)pyrimidine-2,4(1H,3H)-dione) obtained according to WO 96/30346 are dissolved in 90 ml of 0.6 M aqueous HCl at 25° C. The solution is treated with active carbon, filtered and concentrated to dryness keeping an inner temperature of 25-30° C.

60 mL of isopropanol are added to the residue and the suspension is stirred at 25° C. for 24 h before being filtered.

9 g of form III of Tipiracil hydrochloride are obtained (content of residual water according to Karl Fischer titration: 0.31%; content of residual solvents according to GC analysis (head space): 3640 ppm<5000 ppm, ICH limit).

The X-ray diffraction pattern of the obtained product is shown in the FIG. 1. The pattern is consistent with that of form III, having characteristic peaks at diffraction angles of 10.5°, 19.6°, 23.7°, 26.2° and 31.2° (2θ±0.1°).

Comparative Example 1: Preparation of Tipiracil Hydrochloride According to IP.com Journal, 20 June 2017, XP013175208, ISSN: 1533-0001

6N HCl (38 mL) is slowly added to a cooled mixture of 5-chloro-6-[(2-imino-1-pyrrolidinyl)methyl]-2,4(1H,3H)-pyrimidinedione (25 g) in methanol (150 mL), and the resulting reaction mixture is stirred for 45 minutes at 7.5° C. The product isolated by filtration is washed with methanol. After drying, 26.8 g of dry product are obtained.

The content of residual methanol is assessed both through GC (head space), and by NMR analysis. In both cases, the residual amount is 29600 ppm, which is almost 10 times higher than the ICH limit for residual methanol (3000 ppm).

The X-ray diffraction pattern is consistent with that of form III, having characteristic peaks at diffraction angles of 10.5°, 19.6°, 23.7°, 26.2° and 31.2° (2θ±0.1°).

The invention claimed is:

1. Process for the preparation of Tipiracil hydrochloride crystalline form III having a content in solvents compatible with the use as a medicament, said process comprising:
   a) suspending in isopropanol Tipiracil hydrochloride crystalline form II;
   b) stirring the suspension and filtering;
   wherein:
   Tipiracil hydrochloride crystalline form II is a Tipiracil hydrochloride crystalline form having a powder X-ray diffraction pattern showing characteristic peaks at angles of 6.5°, 20.6°, 25.5°, 26.1°, 27.0°, and 30.2° as a diffraction angle (2θ±0.1°); and
   Tipiracil hydrochloride crystalline form III is a Tipiracil hydrochloride crystalline form having a powder X-ray diffraction pattern showing characteristic peaks at angles of 10.5°, 19.6°, 23.7°, 26.2°, and 31.2° as a diffraction angle (2θ±0.1°).

2. The process according to claim 1, wherein the suspension is stirred at a temperature ranging from 0° C. to the boiling point of isopropanol for a time ranging from 1 to 24 hours.

3. The process according to claim 2 wherein the suspension is stirred at a temperature ranging from 20 to 60° C. for a time ranging from 12 to 24 hours.

* * * * *